US00PP20627P2

(12) United States Plant Patent
Perkins

(10) Patent No.: US PP20,627 P2
(45) Date of Patent: Jan. 5, 2010

(54) ***ANGELONIA* PLANT NAMED 'CAR WITTI09'**

(50) Latin Name: *Angelonia angustifolia*
Varietal Denomination: Car Witti09

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/313,047

(22) Filed: Nov. 17, 2008

(51) Int. Cl.
*A01H 5/00* (2006.01)

(52) U.S. Cl. ..... Plt./404

(58) Field of Classification Search ..... Plt./404
See application file for complete search history.

*Primary Examiner*—Kent L Bell
(74) *Attorney, Agent, or Firm*—S. Matthew Edwards

(57) ABSTRACT

A new *Angelonia* plant named 'Car Witti09', particularly distinguished by the white flower color, upright habit, with dense foliage, strong stems, and good floriferousness.

1 Drawing Sheet

Latin name of the genus and species of the plant claimed: *Angelonia angustifolia.*

Varietal denomination: 'Car Witti09'.

BACKGROUND OF THE NEW PLANT

The present invention comprises a new *Angelonia,* botanically known as *Angelonia angustifolia,* and hereinafter referred to by the variety name 'Car Witti09'.

'Car Witti09' is a product of a planned breeding program. The new cultivar 'Car Witti09' has white flower color, more upright habit, with dense foliage, strong stems, and good floriferousness.

'Car Witti09' originated from a hybridization in a controlled breeding program in Gilroy, Calif. USA. The female parent was an unpatented hybrid identified as '319-1' with white color. '319-1' has fewer branches, lighter foliage, and is less floriferiousness than 'Car Witti09'.

The male parent of 'Car Witti09' was an unpatented hybrid seedling identified as '147-1' with white color. '147-1' has fewer branches, lighter foliage, and is less floriferiousness than 'Car Witti09'.

'Car Witti09' was selected as one flowering plant within the progeny of the stated cross in March 2006 in a controlled environment in Gilroy, Calif. USA. The pollination took place in August 2003 and the seed sowing in November 2005.

The first act of asexual reproduction of 'Car Witti09' was accomplished using vegetative cuttings from the initial selection in March 2006 in a controlled environment in Gilroy, Calif. USA.

Horticultural examination of plants grown from cuttings of the plant initiated in March 2006 in Gilroy, Calif. USA, and continuing thereafter, has demonstrated that the combination of characteristics as herein disclosed for 'Car Witti09' are firmly fixed and are retained through successive generations of asexual reproduction.

'Car Witti09' has not been observed under all possible environmental conditions. The phenotype may vary significantly with variations in environment such as temperature, light intensity and day length.

Plant Breeder's Rights for this cultivar were applied for in Canada on Dec. 24, 2007 and in the European Union at CVPO on Aug. 25, 2008. 'Car Witti09' has not been made publicly available more than one year prior to the filing of this application.

DESCRIPTION OF THE DRAWINGS

The accompanying photographic drawing shows typical flower and foliage characteristics of 'Car Witti09' with colors being as true as possible with an illustration of this type. The photographic drawing shows a flowering potted plant of the new variety and a close-up of the flowers. The growing of these plants and photographs took place in Gilroy, Calif. USA in the fall of 2007. The terminal apexes were un-pinched on these plants.

DETAILED BOTANICAL DESCRIPTION

The measurements were taken in Gilroy, Calif. USA, in October 2008 on plants that were growing in 6 inch pots in a greenhouse. These plants were about 4–6 months old.

Color Chart used: Royal Horticultural Society Colour Chart (R.H.S.) 2001

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAR WITTI09' AND A SIMILAR VARIETY

| | 'Car Witti09' | 'Balangwitim' (U.S. Plant Pat. No. 16,501) |
|---|---|---|
| Foliage color | Darker green | Lighter green |
| Flowering response | More floriferiousness | Less floriferiousness |
| Branching habit | Freer branching | Less branching |

Plant:
*Form, growth and habit.*—Upright and vigorous habit, well-branched; pinching 1–2 times after transplant enhances branching.
*Plant height.*—30–35 cm.
*Plant height* (*inflorescence included*).—42–53 cm.
Plant width.—40–45 cm.

Foliage:
*Immature, leaf color, upper surface.*—RHS 146A.
*Lower surface.*—RHS 146A.
*Mature, leaf color, upper surface.*—RHS 147A but a little lighter.
*Lower surface.*—RHS 146A.
*Length.*—6.5–7.0 cm.
*Width.*—0.9–1.3 cm.
*Shape.*—Elliptical.
*Base shape.*—Cuneate.
*Apex shape.*—Acute.
*Margin.*—Serrate.
*Texture.*—Glabrous.
*Color of veins, upper surface.*—RHS 144C.
*Color of veins, lower surface.*—RHS 144C.

Stem:
*Number of main stems per plant.*—5–7.
*Number of leaves per stem* (*before it branches*).—15–18.
*Color of stem.*—RHS 144A.
*Length of stem.*—27–33 cm.
*Diameter.*—0.3 cm.
*Length of internodes.*—2.5–4.0 cm.
*Texture.*—Few glandular hairs.

Inflorescence:
*Type.*—Terminal raceme; florets solitary in leaf axis.
*Number of florets per raceme.*—20–26.
*Raceme length.*—25–30 cm.
*Color of pedicel.*—RHS 144A.
*Length of pedicel.*—1.1–1.2 cm.
*Diameter of pedicel.*—0.05 cm.
*Texture.*—Few glandular hairs.
*Duration of flowering.*—Continuous flowering throughout the summer.
*Lastingness of flowers.*—About 6–7 days.
*Fragrance.*—None.

Corolla:
*Form.*—Single; 5-petaled, fused at base.
*Length of floret.*—2.2–2.4 cm.
*Width of floret.*—2.3–2.4 cm.
*Color upper petals, upper surface.*—RHS N155B but whiter.
*Color upper petals, lower surface.*—RHS 155B but whiter.
*Size upper lip petal length.*—0.7–0.8 cm from corolla opening.
*Size upper lip petal width.*—1.0–1.1 cm.
*Color lower lip, lateral petals, upper surface.*—RHS N155B but whiter.
*Color lower lip, lateral petals, lower surface.*—RHS N155B but whiter.
*Size lower lip, lateral petals length.*—0.9–1.0 cm from corolla opening.
*Size lower lip, lateral petals width.*—0.7–0.8 cm.
*Color lower lip, mid-petal, upper surface.*—RHS N155B but whiter; RHS 144A basally.
*Color lower lip, mid-petal, lower surface.*—RHS N155B but whiter.
*Size lower lip, mid-petal length.*—1.0–1.1 cm from corolla opening.
*Size lower lip, mid-petal width.*—0.9–1.0 cm.
*Petal shape.*—Obovate.
*Apex shape.*—Rounded.
*Margin.*—Entire.
*Petal texture.*—Papillose and a few glandular hairs along the corolla opening.
*Corolla color, inside.*—RHS N155B but whiter; RHS 144A basally and a the base of the filaments.
*Corolla color, outside.*—RHS N155B but whiter; touch of RHS 144A basally.

Bud (just before opening):
*Color.*—RHS 157C.
*Length.*—1.1–1.3 cm.
*Width.*—0.7–0.8 cm.
*Shape.*—Ovate.

Calyx:
*Number of sepals.*—5 fused at base.
*Color of sepals.*—RHS 137B both surfaces.
*Length of sepals.*—0.3–0.4 cm.
*Width of sepals.*—0.1–0.15 cm.
*Sepal shape.*—Lanceolate.
*Apex shape.*—Acute.
*Margins.*—Entire.
*Texture.*—Few glandular hairs.

Reproductive organs:
*Pistil.*—1.
*Length.*—0.3 cm.
*Style color.*—RHS N155B but whiter.
*Stigma color.*—RHS N155B but whiter.
*Number of stamens.*—4, in pairs.
*Color of filaments.*—RHS N155B.
*Length filaments.*—0.4 cm.
*Color of pollen.*—RHS 155A.
*Pollen amount.*—Scarce.
*Fertility/seed set.*—Not observed on this hybrid.

Disease/pest resistance: Disease resistance or susceptibility has not been observed on this hybrid.

What is claimed is:

1. A new and distinct variety of *Angelonia* plant named 'Car Witti09', substantially as illustrated and described herein.

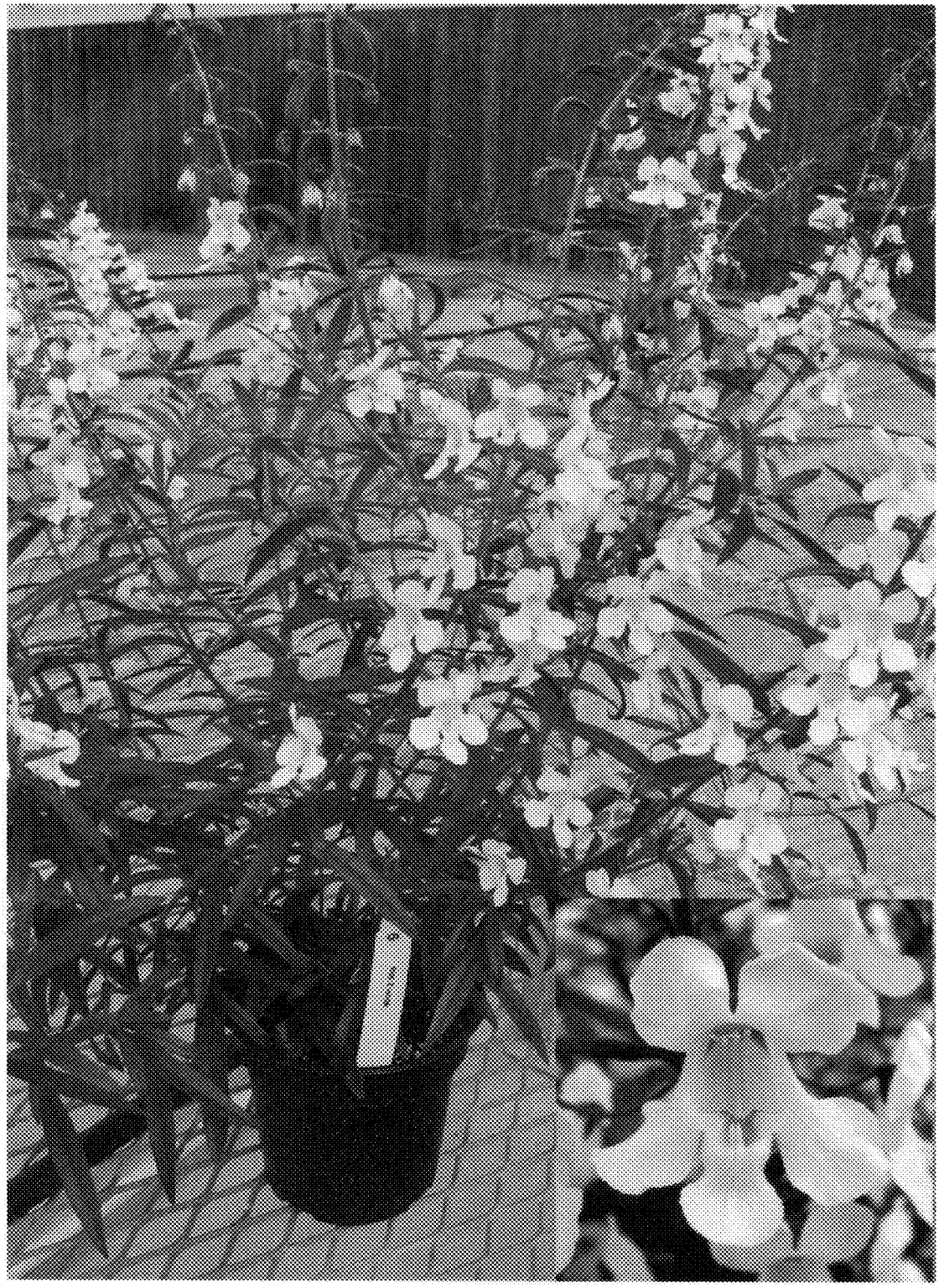

* * * * *